US00PP10284P

United States Patent [19]

Zary

[11] Patent Number: Plant 10,284

[45] Date of Patent: Mar. 17, 1998

[54] FLORIBUNDA ROSE PLANT NAMED 'JACEZZ'

[75] Inventor: Keith W. Zary, Thousand Oaks, Calif.

[73] Assignee: Bear Creek Gardens, Inc., Medford, Oreg.

[21] Appl. No.: 764,732

[22] Filed: Dec. 3, 1996

[51] Int. Cl.[6] ..... A01H 5/00

[52] U.S. Cl. ..... Plt./28

[58] Field of Search ..... Plt./28, 29

[56] References Cited

U.S. PATENT DOCUMENTS

P.P. 2,540 6/1965 de Ruiter ..... Plt./28

*Primary Examiner*—Howard J. Locker

*Attorney, Agent, or Firm*—Klarquist Sparkman Campbell Leigh & Whinston, LLP

[57] ABSTRACT

A new and distinct variety of rose plant of the floribunda class, having attractive, bright red flowers that hold their color very well; dark, glossy green, leathery foliage; resistance to powdery mildew and rust; and a vigorous, upright, well branched habit of growth.

1 Drawing Sheet

The present invention relates to a new and distinct variety of rose plant of the floribunda class which was originated by me by crossing the variety KORholst, U.S. Plant Pat. No. 6,117, with the variety JACcraz, U.S. Plant Pat. No. 3,995. The primary objective of this breeding was to produce a new rose variety having the upright, well branched habit, dark leathery foliage and good petal count of the female parent combined with the very bright red flower and healthy dark green foliage of the male parent. The objective was substantially achieved, along with other desirable improvements, as evidenced by the following unique combination of characteristics that are outstanding in the new variety and that distinguish it from its parents, as well as from all other varieties of which I am aware:

1. Attractive, bright red flowers that hold their color very well;
2. Dark, glossy green, leathery foliage;
3. Resistance to powdery mildew and rust; and
4. Vigorous, upright, well-branched habit of growth.

Asexual reproduction of this new variety by budding, as performed at Wasco, Calif., shows that the forgoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—KORholst.

*Pollen parent.*—JACcraz.

Classification:

*Botanical.*—Floribunda.

*Commercial.*—*Rose hybrida.*

Flower

Observations made from specimens grown in a garden environment at Somis, Calif. in January through September, 1996.

Blooming habit: Recurrent.

Bud:

*Size.*—1½ inches long when the petals start to unfurl.

*Form.*—The bud form is long, pointed ovoid.

*Color.*—When sepals first divide, bud color is Red Group 45A. When half blown, the upper sides of the petals are Red Group 45A; and the lower sides of the petals are Red Group 45A.

*Sepals.*—Color: Green Group 138B. Surface texture: Covered in fine hairs. There are three lightly appendaged sepals. There are two unappendaged sepals with hairy edges.

*Receptacle.*—Color: Green Group 137B—bronze where exposed to bright sun. Shape: Funnel. Size: Medium (7/16 inches × ¼ inches). Surface: Smooth.

*Peduncle.*—Length: Short (2 inches to 2½ inches. Surface: Glandular. Color: Medium green and bronzy. Strength: Stiff, erect.

Bloom:

*Size.*—Medium. Average open size is 3 inches to 3½ inches.

*Borne.*—Singly and several together in clusters of 3 to 5 flowers. If in clusters: Flat.

*Stems.*—Medium, strong. Average length is about 12 inches to 16 inches.

*Form.*—When first open: High centered. Permanence: Flattens, outer petals curl back.

*Petalage.*—Number of petals under normal conditions: 25.

*Color.*—The upper side of the petals is Red Group 45A. The reverse side of the petals is Red Group 45A. The base of each petal has a small (¼ inch × ¼ inch) yellow (Yellow Group 4B) half moon at the point of attachment. The major color on the upper side is Red Group 45A.

*Variegations.*—Occasional white streak on the guard petals.

*Discoloration.*—The general tonality at the end of the first day: No change. At the end of the third day: No change. By day 5, there is some fading of the petals to Red Group 45C. By day 6 or 7, petal drop has occurred.

*Fragrance.*—Slight.
*Texture.*—Thick.
*Shape.*—Round.
*Form.*—Tips slightly recurved, edges slightly quilled.
*Arrangement.*—Imbricated, with few, small petaloids in the center.
*Persistence.*—Drop off cleanly.
*Lastingness.*—On the plant: Fair (5 or 6 days). As a cut flower: Fair (7 days).

Reproductive parts:
*Anthers.*—Size: Medium. Quantity: Many. Color: Reddish brown. Arrangement: Regular around styles.
*Filaments.*—Color: Yellow.
*Pollen.*—Color: Lemon yellow.
*Styles.*—Color: Red.
*Stigmas.*—Color: Greenish white.

Form: Bush.

Growth: Very vigorous, upright, branching. Height at one year of age, without pruning is 3½ feet; width is 3 feet.

Foliage:
*Number of leaflets on normal mid-stem leaves.*—7 or 5.
*Size.*—Large (6 inches × 3½ inches).
*Quantity.*—Abundant.
*Color.*—New foliage: Both surfaces Greyed Red Group 178A. Old foliage: Upper surface: Green Group 136A; Lower surface: Green Group 136C.

Leaflets:
*Shape.*—Pointed.
*Texture.*—Upper side: Leathery, glossy.
*Edge.*—Serrated.
*Serration.*—Single, small.
*Petiole rachis.*—Color: Reddish.
*Petiole underside.*—Smooth with occasional prickles.
*Stipules.*—Medium (½ inch), serrated.
*Disease resistance.*—Resistant to mildew and rust under normal growing conditions at Somis, Calif.

Wood:
*New wood.*—Color: Reddish. Bark: Smooth.
*Old wood.*—Color: Green. Bark: Smooth.

Prickles:
*Quantity*: On main canes from base: Ordinary. On laterals from main canes: Ordinary.
*Form.*—Medium (5/16"), hooked downward.
*Color when young.*—Red.

Small prickles:
*Quantity.*—On main stalks : None. on laterals: None.

I Claim:

1. A new and distinct variety of rose plant of the floribunda class, substantially as herein shown and described, characterized particularly as to novelty by the unique combination of its attractive, bright red flowers that hold their color very well; dark, glossy green, leathery foliage; resistance to powdery mildew and rust; and vigorous, upright, well branched habit of growth.

* * * * *

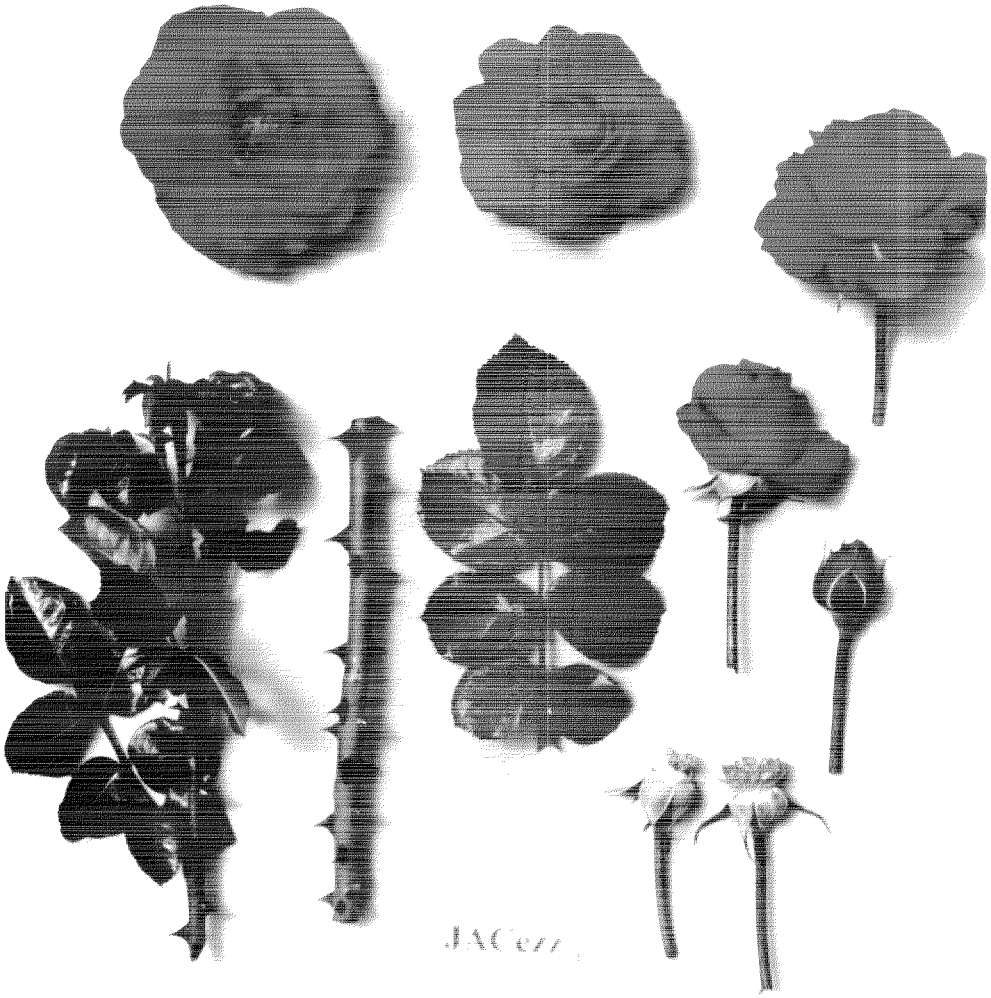
JACezz